(12) United States Patent
Lee et al.

(10) Patent No.: US 8,778,152 B2
(45) Date of Patent: Jul. 15, 2014

(54) SENSOR USED TOGETHER WITH A DETECTOR TO MEASURE BIOMATERIAL, AND APPARATUS USING SAME

(75) Inventors: Jin-Woo Lee, Gyeonggi-do (KR); Jae-Kyu Choi, Daejeon (KR); Tae-Hun Kim, Gyeonggi-do (KR); Young-Il Yoon, Gyeonggi-do (KR)

(73) Assignee: CERAGEM MEDISYS Inc., Gyeonggi-do (KR)

( * ) Notice: Subject to any disclaimer, the term of this patent is extended or adjusted under 35 U.S.C. 154(b) by 0 days.

(21) Appl. No.: 13/376,720

(22) PCT Filed: Apr. 30, 2010

(86) PCT No.: PCT/KR2010/002755
§ 371 (c)(1),
(2), (4) Date: Dec. 7, 2011

(87) PCT Pub. No.: WO2011/002152
PCT Pub. Date: Jan. 6, 2011

(65) Prior Publication Data
US 2012/0073968 A1 Mar. 29, 2012

(30) Foreign Application Priority Data
Jun. 30, 2009 (KR) .................. 10-2009-0059190

(51) Int. Cl.
*G01N 27/327* (2006.01)
*G01N 33/66* (2006.01)

(52) U.S. Cl.
USPC ............ 204/403.02; 204/403.04; 204/403.13; 204/403.14

(58) Field of Classification Search
CPC ... G01N 27/327; G01N 27/416; G01N 27/49; G01N 27/3271; G01N 33/48; G01N 33/483; G01N 33/487; G01N 33/48707; G01N 33/49; G01N 33/492; G01N 33/50; G01N 33/60

USPC ............ 204/403.01–403.15; 205/777.5, 778, 205/792; 435/4–40.52; 422/68.1–98; 436/62–71, 500–548

See application file for complete search history.

(56) References Cited

U.S. PATENT DOCUMENTS 8,247,233 B2* 8/2012 Gofman et al. ............... 436/48
2002/0177763 A1* 11/2002 Burns et al. .................. 600/345

(Continued)

FOREIGN PATENT DOCUMENTS

| JP | 2008-544296 A | 12/2008 |
| WO | 2009/022779 A1 | 2/2009 |

OTHER PUBLICATIONS

International Search Report issued in PCT/KR2010/002755, mailed on Jan. 21, 2011, with translation, 7 pages.

(Continued)

*Primary Examiner* — Susan D Leong
(74) *Attorney, Agent, or Firm* — Osha Liang LLP

(57) ABSTRACT

The present invention relates to a sensor used together with a detector to measure biomaterial, and to an apparatus using same. A sensor of the present invention comprises: a body portion with a three-dimensional shape, having a biomaterial introduction hole, and attachable and detachable to/from a detector; a sensor portion with a plurality of reaction electrodes formed on one surface thereof, and a plurality of transfer electrodes formed on the other surface thereof; and an analyzer reagent fixed above the reaction electrodes. The sensor portion, together with the body portion, forms a reaction chamber connected to the biomaterial introduction hole, and is attached to the body portion such that the reaction electrodes are oriented toward the reaction chamber. According to the present invention, attachment and detachment is easy, even for the elderly, and the contamination of the sensor can be minimized.

14 Claims, 7 Drawing Sheets

(56) References Cited

U.S. PATENT DOCUMENTS

| | | | |
|---|---|---|---|
| 2003/0180824 A1* | 9/2003 | Mpock et al. | 435/13 |
| 2003/0212344 A1 | 11/2003 | Yuzhakov et al. | |
| 2004/0197231 A1* | 10/2004 | Katsuki et al. | 422/68.1 |
| 2004/0209350 A1* | 10/2004 | Sakata | 435/287.1 |
| 2005/0011759 A1* | 1/2005 | Moerman et al. | 204/403.03 |
| 2005/0083527 A1* | 4/2005 | Flaherty et al. | 356/437 |
| 2005/0240119 A1* | 10/2005 | Draudt et al. | 600/583 |
| 2006/0042080 A1* | 3/2006 | Say et al. | 29/876 |
| 2006/0243589 A1* | 11/2006 | Doi et al. | 204/403.01 |
| 2009/0163367 A1 | 6/2009 | Yoo | |

OTHER PUBLICATIONS

Written Opinion issued in PCT/KR2010/002755, mailed on Jan. 21, 2011, 3 pages.

* cited by examiner (a)

(b)

(a)

(b)

(c)

SENSOR USED TOGETHER WITH A DETECTOR TO MEASURE BIOMATERIAL, AND APPARATUS USING SAME

TECHNICAL FIELD

The present invention relates to a sensor used with a detector to measure a biomaterial and an apparatus using the same, and more particularly, a biomaterial measuring sensor and a measuring apparatus using the same that are capable of enabling easy attachment and detachment even when a user with poor vision or mobility uses the sensor and minimizing contamination of the sensor.

BACKGROUND ART

A biosensor is a measuring apparatus for investigating properties of a material using functions of an organism. Since the biosensor uses a biomaterial as a detection element, sensitivity and reaction specificity are good. Accordingly, the biosensor is widely used in various fields such as clinical chemistry assay of medical/medicine fields, process measurement of bio industries, environment measurement, stability estimation of chemicals, and so on, and its range is being continuously enlarged. In particular, in a medicine diagnosis field, the biosensors are widely used to analyze a sample including a bio-sample. The biosensors are divided into enzyme assay biosensors and immunoassay biosensors according to the kind of detecting element, and into optical biosensors and electrochemical biosensors according to a method of quantitatively analyzing a target material within a bio-sample.

The enzyme assay biosensors are designed to use a specific reaction between an enzyme and a substrate and a specific reaction between an enzyme and an enzyme inhibitor, and the immunoassay biosensors are designed to use a specific reaction between an antigen and an antibody.

The optical biosensors are widely used to measure a concentration of a target material by measuring transmittance, absorbance, or alteration in wavelength. The optical biosensors have an advantage in that, since reaction mechanisms of various materials to be analyzed have already been known and measurement is made after a reaction takes place for a sufficient time, a deviation in measurement time is low. In contrast, the optical biosensors have a disadvantage in that they require a longer measurement time and a greater quantity of samples than the electrochemical biosensors. Further, the optical biosensors have other disadvantages in that measured results are influenced by turbidity of a sample, and it is difficult to miniaturize an optical unit.

The electrochemical biosensors are used to measure a concentration of a target material by measuring an electric signal obtained from a reaction. The electrochemical biosensors have advantages in that it is possible to amplify a signal using a very small quantity of sample, they are easy to miniaturize, it is possible to stably obtain a measured signal, and they can be easily combined with a telecommunication instrument. However, the electrochemical biosensors have disadvantages in that an electrode manufacturing process is additionally required, the cost of production is high, and a measured signal is very sensitive to response time.

Meanwhile, the conventional biosensor generally has a planar strip structure. A user needs to insert the bio sensor having a planar strip structure into a narrow slit of a detector, for example, when blood sugar is measured using the biosensor. However, for example, since many diabetic and elderly patients have poor vision, it is difficult to insert the biosensor having a planar strip structure into the narrow slit. In addition, when the biosensor is removed from the detector after measurement of the blood sugar, the user grips around a portion of the biosensor stained with the blood and extracts and wastes the biosensor. At this time, since the user's finger is likely to be stained with blood, the user may feel uncomfortable. In addition, the conventional strip type biosensor may be easily contaminated when the biosensor is inserted into the detector by the user.

DISCLOSURE

Technical Problem

In order to solve the foregoing and/or other problems, it is an objective of the present invention to provide a biosensor that can be easily attached and detached by a user with poor vision.

In addition, it is another objective of the present invention to provide a biosensor capable of minimizing contamination of the sensor from the outside.

The objectives of the present invention are not limited to those mentioned above. Other objectives and advantages of the present invention which are not disclosed will be understood from the following description, and be apparent with reference to the embodiments of the present invention. Also, it is obvious to those skilled in the art that the objectives and advantages of the present invention will be realized by the means as claimed and combinations thereof.

Technical Solution

In order to achieve the above objectives, according to one aspect of the present invention, there is provided a biomaterial measuring sensor used with a detector to measure a biomaterial, which includes: a body portion having a three-dimensional shape and a biomaterial introduction hole, and attached to and detached from the detector; a sensor portion having one surface on which a plurality of reactive electrodes configured to cause a biochemical reaction with the biomaterial are formed and the other surface on which a plurality of conductive electrodes configured to transmit a signal generated by the biochemical reaction to the detector are formed; and a reaction reagent fixed onto the reactive electrodes and biochemically reacting with the biomaterial, wherein the sensor portion is attached to the body portion such that the sensor portion forms a reaction chamber connected to the biomaterial introduction hole with the body portion and the reactive electrodes are directed to the reaction chamber.

According to another aspect of the present invention, there is provided a biomaterial measuring apparatus including a detector and a measuring sensor, wherein the measuring sensor includes: a body portion having a three-dimensional shape and a biomaterial introduction hole, and attached to and detached from the detector; a sensor portion having one surface on which a plurality of reactive electrodes configured to cause a biochemical reaction with the biomaterial are formed and the other surface on which a plurality of conductive electrodes configured to transmit a signal generated by the biochemical reaction to the detector are formed; and a reaction reagent fixed onto the reactive electrodes and biochemically reacting with the biomaterial, wherein the sensor portion is attached to the body portion such that the sensor portion forms a reaction chamber connected to the biomaterial introduction hole with the body portion and the reactive electrodes are directed to the reaction chamber, wherein the detector comprises a connector electrically connected to the conductive electrodes when the body portion is attached to the detector.

Advantageous Effects

According to the present invention, a biomaterial measuring apparatus in accordance with the present invention can be easily used by a user with poor vision. In addition, the biomaterial measuring apparatus in accordance with the present invention can minimize contamination of a sensor from the outside.

MODE FOR INVENTION

The objects, features, and advantages of the present invention will be apparent from the following detailed description of embodiments of the invention with references to the following drawings. Descriptions of well-known components and processing techniques are omitted so as not to unnecessarily obscure the embodiments of the present invention. The following terms are defined in consideration of functions of the to present invention and may be changed according to users or operator's intentions or customs. Thus, the terms shall be defined based on the contents described throughout the specification. Hereinafter, embodiments of the present invention will be described in detail with reference to the accompanying drawings.

Figure 1:
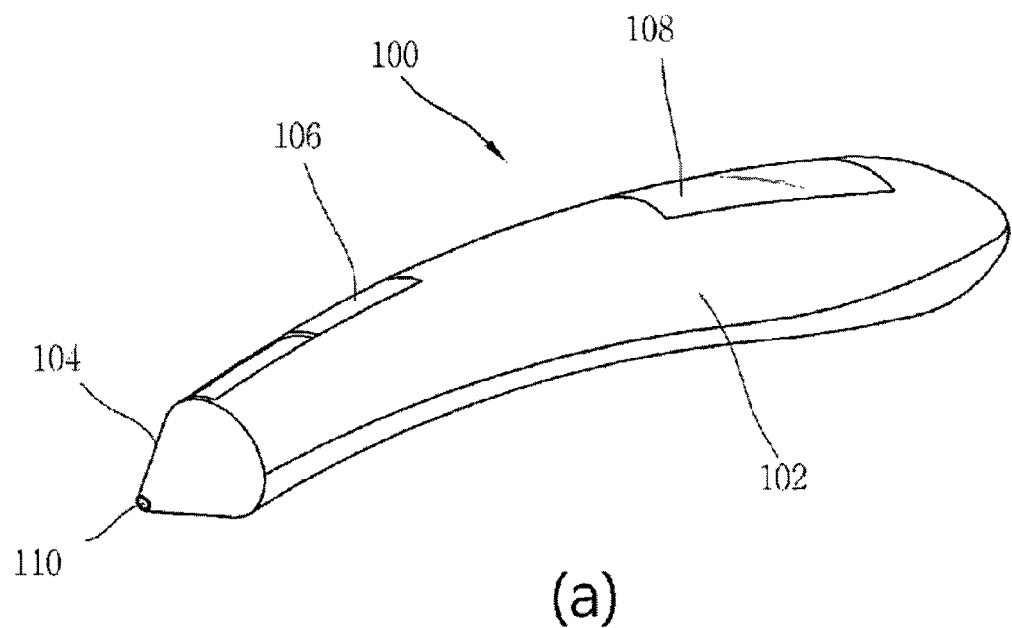
FIG. 1A is a view for explaining a biomaterial measuring apparatus in accordance with an embodiment of the present invention.
FIG. 1B is a view for explaining a state in which a biosensor is detached from a detector of the biomaterial measuring apparatus of FIG. 1A.
Figure 1:
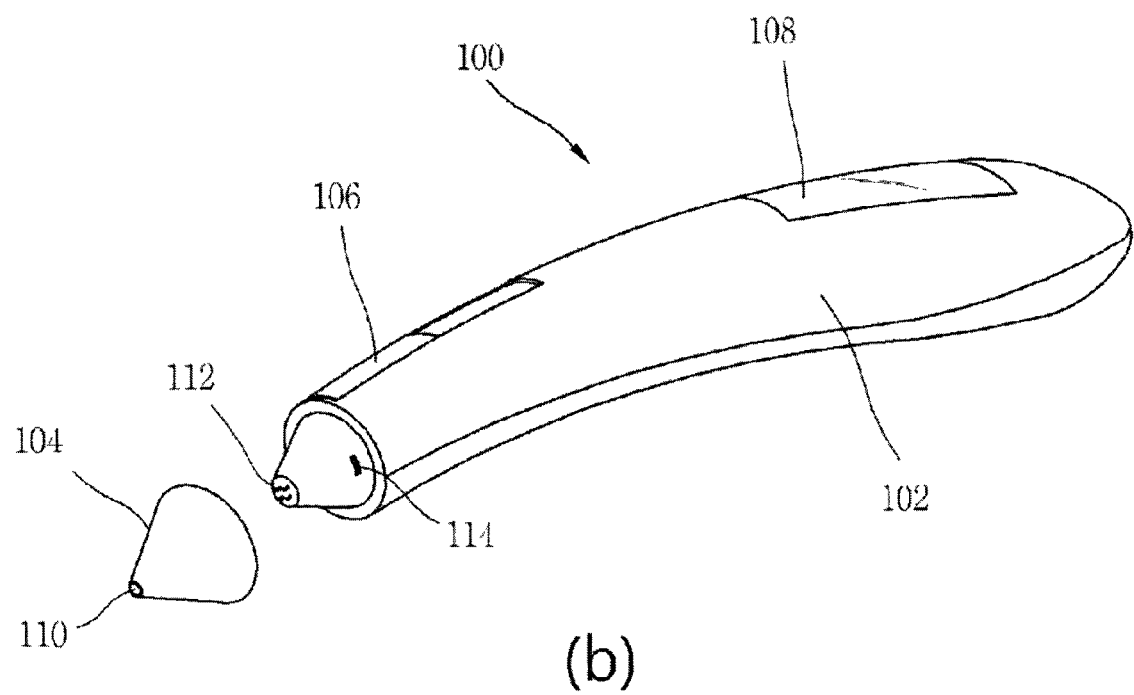

FIG. 1A is a view for explaining a biomaterial measuring apparatus in accordance with an embodiment of the present invention, and FIG. 1B is a view for explaining a state in which a biosensor is detached from a detector of the biomaterial measuring apparatus of FIG. 1A.

As shown, a biomaterial measuring apparatus 100 includes a detector 102 and a three-dimensional (3D) biosensor 104. The detector 102 and the biosensor 104 are attached to each other through a concavo-convex structure. FIGS. 1A and 1B show the biomaterial measuring apparatus 100 in which the biosensor 104 and the detector 102 are fastened to each other in the concavo-convex structure, for example, such that a projection of the detector 102 is inserted into a groove formed in the biosensor 104. On the other hand, the detector and the biosensor may be fastened to each other such that a projection of the biosensor is inserted into a groove formed in the detector. When the biosensor and the detector are attached to each other in the concavo-convex structure, there is no need for an additional manufacturing process for forming the concavo-convex structure, and the biosensor and the detector are fastened to each other by a mechanical force. In addition, the fastened state can be easily released by the mechanical force of the detector to enable easy attachment and detachment.

The detector and the biosensor may be aligned with and attached to each other by a magnetic force. For this, the detector may include a permanent magnet or an electromagnet adjacent to or around a connector 112. When the electromagnet is used, an ejector button 106 may be configured to cut power supplied to the electromagnet to demagnetize the electromagnet such that the biosensor is detached from the detector. In order to be attached to or detached from the detector, the permanent magnet may have a weak magnetic force. When the permanent magnet is used, the permanent magnet may be installed at the detector, and a paramagnet may be installed at the biosensor.

The biosensor 104 introduces a biomaterial through a biomaterial introduction hole 110, and generates an electrical signal by a biochemical reaction between a reagent contained in the biosensor 104 and the introduced biomaterial to transmit the signal to the detector 102. The reagent may include an enzyme, etc., which causes a biochemical reaction with the introduced biomaterial. The detector 102 analyzes the electrical signal transmitted from the biosensor 104 using a built-in microprocessor (not shown), measures a concentration of an analysis material contained in the introduced biomaterial, for example, blood sugar, and displays the concentration of the analysis material through a display 108. After measuring the concentration of the analysis material, a user pushes or presses the ejector button 106 to detach the biosensor 104 from the detector 102.

As shown in FIG. 1B, a groove 114 is formed in a portion of the detector 102 to which the biosensor 104 is attached, and a hook (not shown) fastened to the groove 114 is formed at the bio sensor 104. The connector 112 is electrically connected to the biosensor 104 to provide the electrical signal transmitted from the biosensor 104 to the microprocessor for signal analysis built in the detector 102. A resilient body (not shown) configured to provide a resilient force in a direction in which the biosensor 104 is attached to the detector 102 is installed at an opposite portion of the connector 112 electrically connected to the biosensor 104. The resilient body functions to further attach the connector 112 to the biosensor 104. In addition, even when the detector 102 and the biosensor 104 are attached to each other in the concavo-convex structure, the electromagnet or permanent magnet may be installed at or around the connector 112. The permanent magnet may have a weak magnetic force such that the bio sensor 104 can be detached from the detector 102 easily after measuring the concentration of the analysis material.

Figure 2:
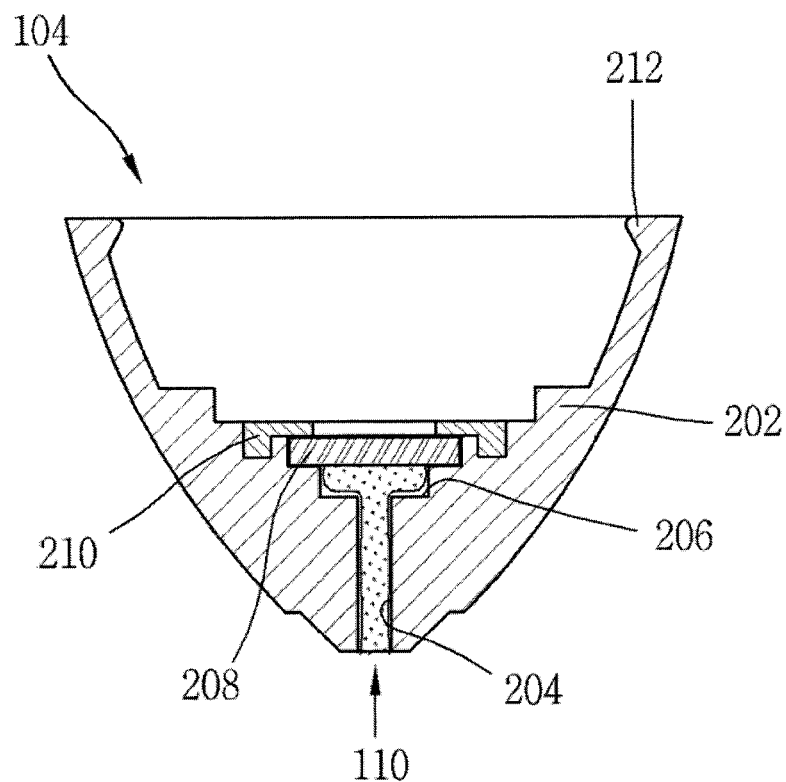
FIG. 2 is a side cross-sectional view of the biosensor in accordance with an embodiment of the present invention.

FIG. 2 is a side cross-sectional view of the biosensor in accordance with an embodiment of the present invention.

A body portion 202 is inserted into a portion of the detector 102, at which the connector 112 is formed, so that the biosensor 104 is attached to the detector 102. An inner shape of the body portion 202 may be the same as an outer shape of the portion of the detector 102 to which the bio sensor 104 is attached. The body portion 202 may have a 3D shape, for example, a hollow conical or pyramidal shape, which can be fastened to the detector 102 and stacked to be packed.

Figure 3:
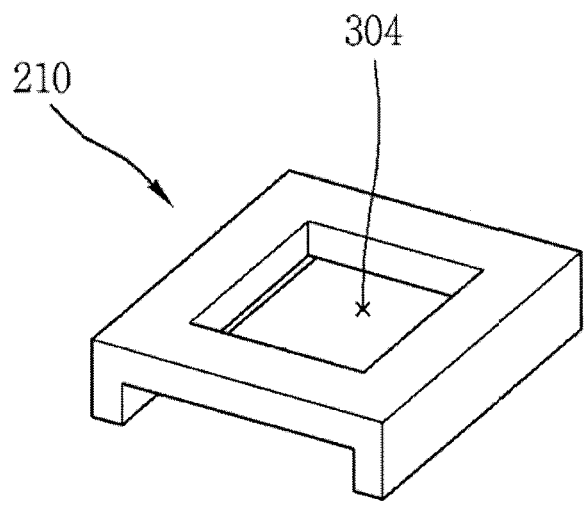
FIG. 3 is a view for explaining a structure of a sensor fixing portion of FIG. 2.

A sensor fixing portion 210 fixes the sensor portion 208 to the body portion 202. FIG. 3 is a view for explaining a structure of the sensor fixing portion 210. The sensor fixing portion 210 has a hole 304 formed therein to electrically connect a conductive electrode of the sensor portion 208 to a connector 112 of the detector 102. A hook 212 is fastened to the groove 114 of the detector 102 when the biosensor 104 is attached to the detector 102 such that the biosensor 104 can be stably attached to the detector 102. The sensor fixing portion 210 may be formed of a hot-melt film. In addition, the sensor fixing portion 210 may be fixed to the body portion 202 through fusion only, or fixed to the body portion 202 through assembly only without fusion.

As shown in FIG. 2, a reaction chamber 206 is connected to the biomaterial introduction hole 110 through a sample path 204. The sample path 204 is formed as a capillary tube such that a sample can be easily introduced into the reaction chamber 206. A biomaterial such as blood is introduced into the biomaterial introduction hole 110 by a capillary phenomenon by the sample path 204 and introduced into the reaction chamber 206.

The biomaterial introduction hole 110 may have a projection shape to prevent introduction of the biomaterial from being blocked due to the biomaterial introduction hole 110 being completely blocked by a user's finger, for example, when the finger touches the biomaterial introduction hole 110 to introduce the blood into the biosensor 104. When the body portion 202 has a conical or pyramidal shape, the biomaterial introduction hole 110 corresponds to an apex of the conical or pyramidal shape.

A surface of the sensor portion 208 facing the reaction chamber 206 has a plurality of reactive electrodes (not shown), and a reactive reagent is fixed across the reactive electrodes. The reactive reagent causes a biochemical reaction with the biomaterial introduced into the reaction chamber 206 to generate an electrical signal, and the generated electrical signal is transmitted to the reactive electrode. The electrical signal transmitted to the reactive electrode is transmitted to the detector 102 through a plurality of conductive electrodes formed at the other surface of the sensor portion 208. The sensor portion 208 is attached to the body portion 202 such that the sensor portion 208 forms the reaction chamber 206 with the body portion 202 and the plurality of reactive electrodes (not shown) formed at one surface are directed to the reaction chamber 206.

Figure 4:
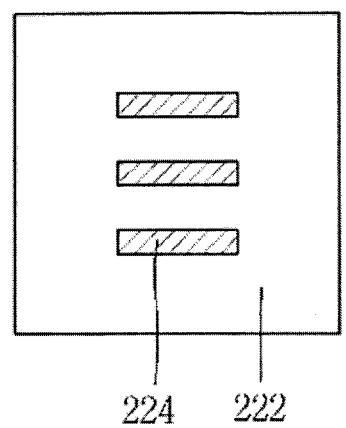
FIGS. 4A to 4C are views for explaining a structure of the sensor portion of FIG. 2.
Figure 4:
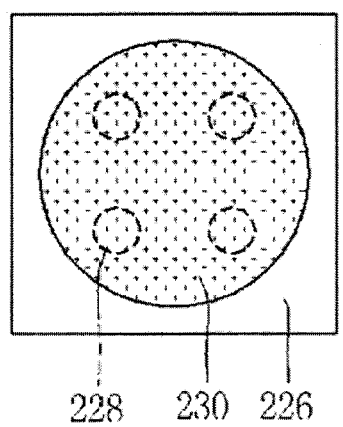
Figure 4:
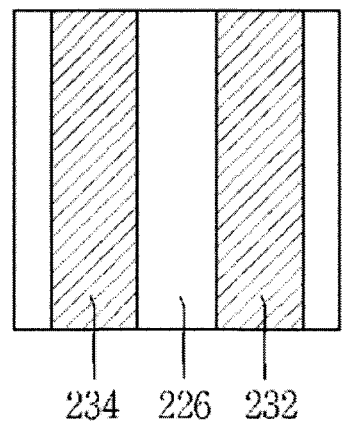

FIGS. 4A to 4C are views for explaining a structure of the sensor portion of FIG. 2. FIG. 4A shows a rear surface of an automatic coding sensor portion, FIG. 4B shows a front surface of a measuring sensor portion, and FIG. 4C shows a rear surface of the measuring sensor portion. Sensor portions 222 and 226 may be easily manufactured by a typical thin film deposition technique, plating technique, printing electronic technique, and so on, and may be easily manufactured using a printed circuit board (PCB).

In FIG. 4A, electrodes 224 formed at the rear surface of the automatic coding sensor portion 222 inform the detector 102 that the current biosensor attached to the detector is provided for automatically coding, and characteristics of the biosensor 104 attached to the detector 102 are to be used to measure the biomaterial using a resistance value. The reactive electrode or the reactive reagent is not formed at a front surface of the sensor portion facing the reaction chamber 206 because it is not provided to measure the biomaterial.

As shown in FIG. 4B, a plurality of reactive electrodes 228 are formed at a front surface of the measuring sensor portion 226 directed to the reaction chamber 206, and a reaction reagent 230 configured to cause a biochemical reaction with an analysis material to generate an electrical signal is fixed onto the reactive electrodes 228. As shown in FIG. 4C, conductive electrodes 232 and 234 configured to transmit the electrical signal generated through the biochemical reaction to the detector 102 are formed at a rear surface of the measuring sensor portion 226. The reactive electrode 228 and the conductive electrodes 232 and 234 are electrically connected to each other through a conductor (not shown) passing through the sensor portion 226.

FIGS. 5A to 5E are views showing a sequence of using the biomaterial measuring apparatus in accordance with the present invention.

Figure 5:
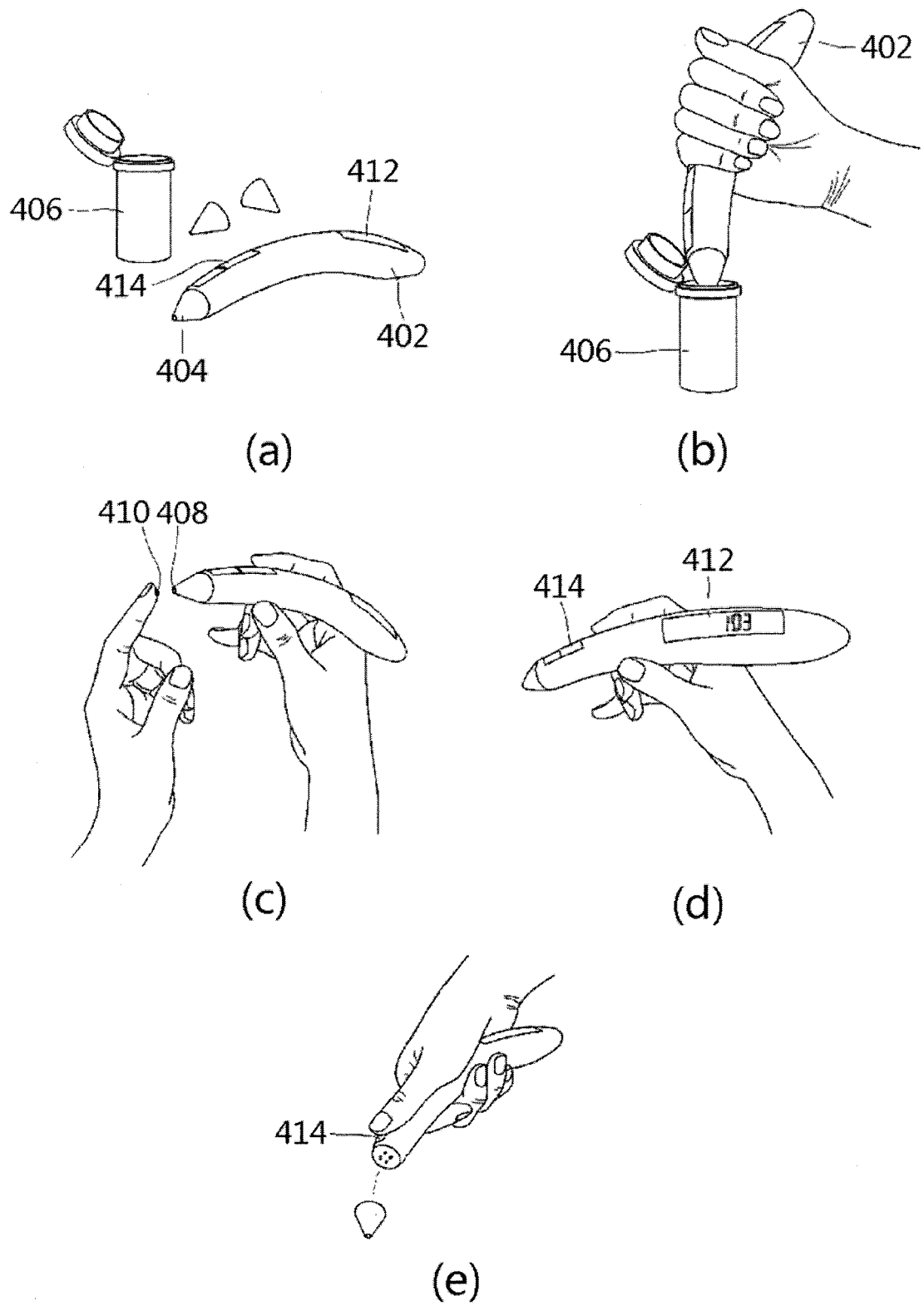
FIGS. 5A to 5E are views for explaining a sequence of using the biomaterial measuring apparatus in accordance with the present invention.

First, as shown in FIG. 5A, a user prepares a detector 402 and a biosensor 404. The detector 402 includes a display 412 configured to display a measurement result, and an ejector 414 configured to detach a used biosensor 404. The display 412 may include a liquid crystal display (LCD), a light emitting diode (LED), and so on. The biosensor 404 is stacked and stored in a case 406. Next, the user attaches the uppermost biosensor stacked in the case 406 to the detector 402 as the detector 402 to which the connector 112 (see FIG. 1) is exposed is inserted into the case 406. As described above, in order to easily align and attach the biosensor to the detector 402, a magnetic material may be installed at or around the connector.

Next, as shown in FIG. 5C, the user draws blood 410 from his/her finger to introduce the blood into the biosensor through a biomaterial introduction hole 408. When the finger contacts the biomaterial introduction hole 408, the blood is introduced into the biosensor to the reaction chamber 206 (see FIG. 2) by a capillary phenomenon. The blood introduced into the biosensor causes a biochemical reaction with a reaction reagent to generate an electrical signal, and the generated electrical signal is analyzed by the detector 402 to calculate a concentration of a material to be analyzed. As shown in FIG. 5D, the calculated concentration of the material to be analyzed is displayed to the user through the display 412. The user who checked the concentration of the material to be analyzed through the display 412 detaches the attached biosensor from the detector 402 using an ejector button 414.

According to the embodiment, when the detector 402 and the biosensor 404 are used, since the biosensor can be simply fitted onto a front portion of the detector 402, rather than inserting the conventional biosensor into a narrow slit of the detector, the user can easily attach the biosensor to the detector. In addition, when the case 406 in which the biosensors are stacked is used or a magnet is installed at or around the connector of the detector 402, the biosensor can be more easily attached to the detector. Since the biosensor can be easily attached to the detector, contamination of the biosensor during attachment of the biosensor can be effectively prevented.

In addition, according to the embodiment, even when the detector 402 has no ejector function, since the biosensor has a 3D shape, the user can easily detach the biosensor from the detector. When the detector has an ejector function, since the biosensor can be simply detached by pushing or pressing the ejector button 414 with no need to grip the biosensor with the fingers, the biosensor can be more easily detached from the detector. In addition, since there is no need to manually grip the sensor strip stained with blood and extract the sensor strip from the detector after measurement as described in the related art, there is no probability of staining the fingers with blood.

Figure 6:
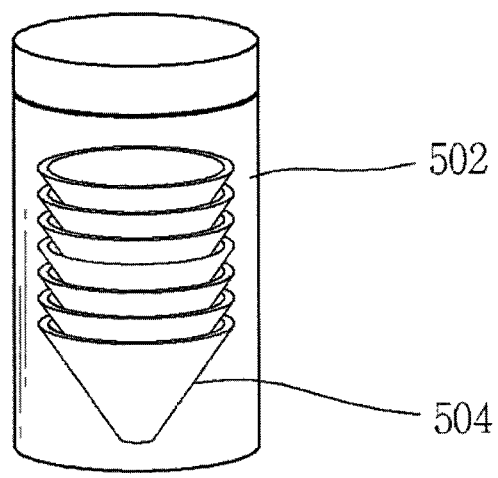
FIG. 6 is a view for explaining a state in which biosensors are accommodated in a sensor case.

FIG. 6 is a view for explaining a state in which biosensors are accommodated in a sensor case. As shown in FIG. 6, biosensors 504 having a 3D shape are accommodated in a sensor case 502 in a state in which a portion of the biosensor attached to or detached from the detector 102 is directed upward to be easily attached to the detector 102. In addition, in order to accommodate a large number of biosensors 504 in a limited space of the sensor case 502, the biosensors 504 are accommodated in the sensor case 502 in an overlapped state.

Figure 7:
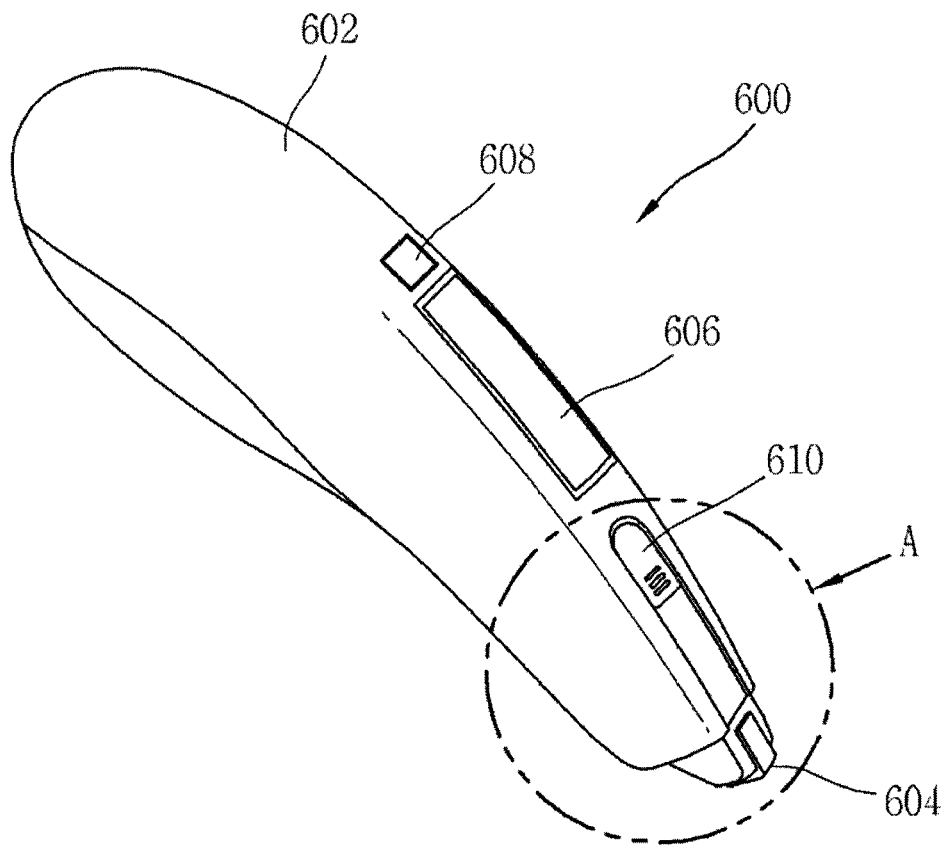
FIG. 7 is a view for explaining a biomaterial measuring apparatus in accordance with another embodiment of the present invention.
Figure 8:
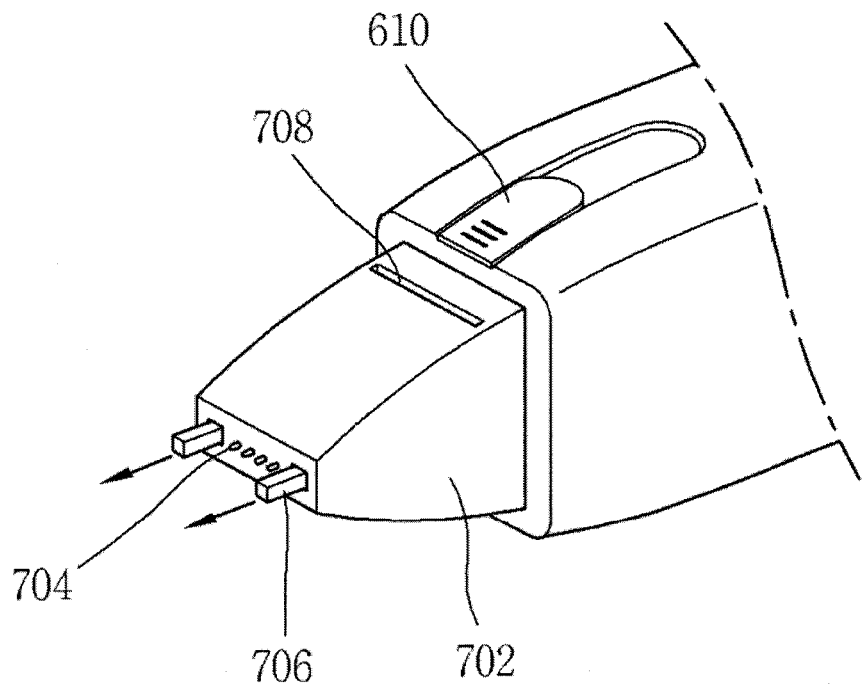
FIG. 8 is a view for explaining a structure of a detector from which a biosensor is detached, enlarging a portion A of FIG. 7.

FIG. 7 is a view for explaining a biomaterial measuring apparatus 600 in accordance with another embodiment of the present invention. FIG. 8 is a view for explaining a structure of a detector 602 of a portion A, from which a biosensor 604 is detached, and FIG. 9 is a view for explaining a structure of the biosensor 604.

As shown in FIG. 7, the biomaterial measuring apparatus 600 includes a detector 602 and a biosensor 604. The biosensor 604 introduces a biomaterial through a biomaterial introduction hole 802, and generates an electrical signal through a biochemical reaction between a reagent contained in the biosensor 604 and the introduced biomaterial to transmit the electrical signal to the detector 602. A reaction reagent includes an enzyme, etc., causing a biochemical reaction with the introduced biomaterial. The detector 602 analyzes the electrical signal transmitted from the biosensor 604 using a built-in microprocessor (not shown) according to an input of an operation button 608, measures a concentration of an analysis material contained in the introduced biomaterial, and displays the concentration of the analysis material through a display 606. When the user pushes or presses an ejector button 610 after measuring the concentration of the analysis material, an ejector 706 is extracted to detach the biosensor 604 from the detector 602.

As shown in FIG. 8, a groove 708 is formed at a portion 702 of the detector 602 to which the biosensor 604 is attached, and a hook 804 fastened to the groove 708 is formed at the biosensor 604. A connector 704 is electrically connected to the biosensor 604 to provide the electrical signal transmitted from the biosensor 604 to the signal analysis microprocessor built in the detector 602. A resilient body (not shown) configured to provide a resilient force in a direction in which the biosensor 604 is attached to the detector 602 may be installed at an opposite portion of the connector 704 electrically connected to the biosensor 604. The resilient body further attaches the connector 704 to the biosensor 604. In addition, the detector 602 may have a magnet (not shown) installed at or around the connector 704. The magnet helps the biosensor 604 attach to an appropriate position of the detector 602.

Figure 9:
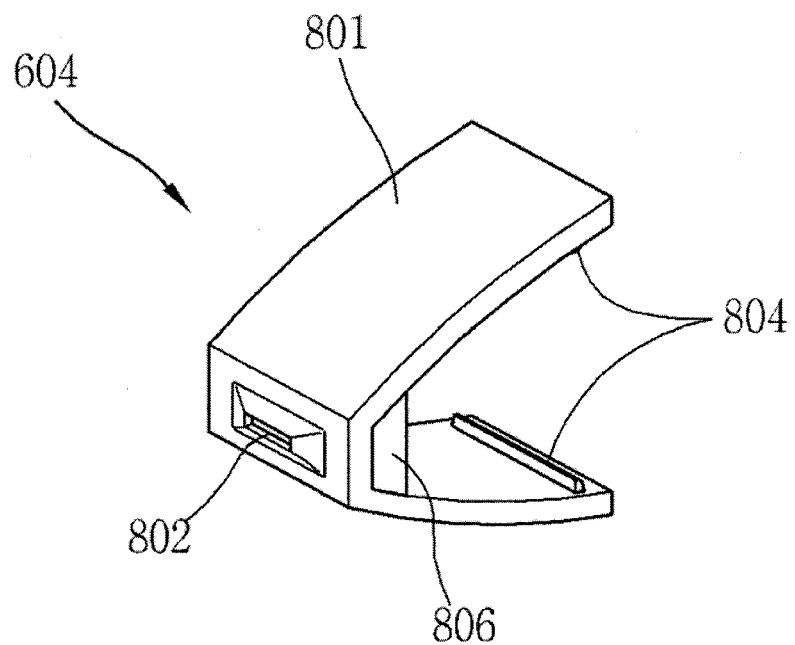
FIG. 9 is a view for explaining a structure of a biosensor in accordance with another embodiment of the present invention.

In FIG. 9, the body portion 801 is inserted into a portion of the detector 602 at which the connector 704 is formed, such that the biosensor 604 is attached to the detector 602. The body portion 801 may be formed of a plastic material having a certain level of resilient force. An inner shape of the body portion 801 is the same as an outer shape of a portion of the detector 602 to which the biosensor 604 is attached. The body portion 801 has an open trapezoidal shape. The hook 804 is fastened to the groove 708 of the detector 602 when the biosensor 604 is attached to the detector 602 so that the biosensor 604 is stably attached to the detector 602.

The biomaterial introduction hole 802 is connected to a sensor portion 806 via a sample path (not shown) and a reaction chamber (not shown). The sample path is formed of a capillary tube such that a sample can be easily introduced into the reaction chamber. Since the biomaterial introduction hole 802 is completely blocked by a finger, for example, when the finger contacts the biosensor 604 to introduce blood into the biosensor 604, the biomaterial introduction hole 802 may have a projection shape to prevent introduction of the biomaterial from being blocked. The biomaterial introduction hole 802 is formed at an upper narrow side of the body portion 801.

A plurality of reactive electrodes (not shown) are formed at a surface of the sensor portion 806 facing the biomaterial introduction hole 802 (or the reaction chamber), and a reactive reagent is fixed across the reactive electrodes. The reactive reagent causes a biochemical reaction with the biomaterial introduced into the reaction chamber to generate an electrical signal, and the generated electrical signal is transmitted to the reactive electrodes. The electrical signal transmitted to the reactive electrodes is transmitted to the detector 602 through a plurality of conductive electrodes formed at the other surface of the sensor portion 806. The sensor portion 806 is attached to the body portion 801 to form the reaction chamber with the body portion 801 such that the plurality of reactive electrodes (not shown) formed at one surface thereof are directed to the reaction chamber. The sensor portion 806 may be adhered to the body portion 801 by an adhesive or may be fused to the body portion 801 by heat.

Figure 10:
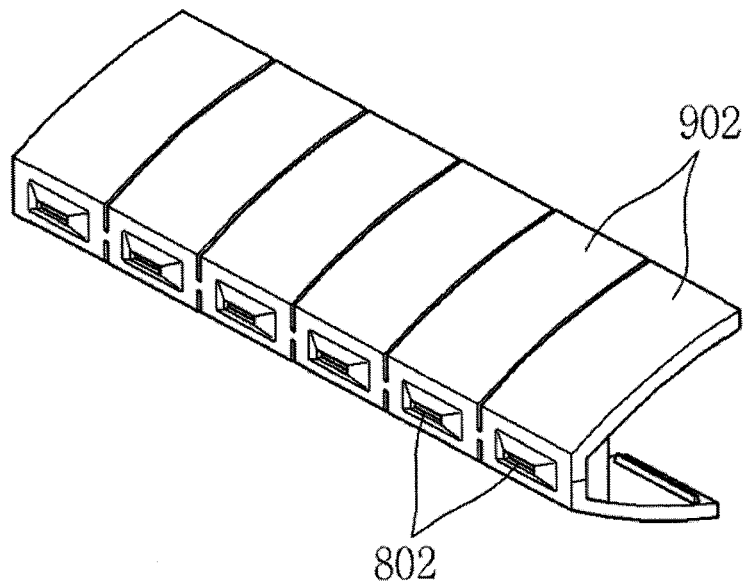
FIG. 10 is a view for explaining a shape of a plurality of biosensors manufactured according to another embodiment of the present invention.

FIG. 10 is a view for explaining a shape of a plurality of biosensors shown in FIG. 9, which are manufactured simultaneously. As shown, for example, when 10 biosensors are manufactured in a shape in which side surfaces of the biosensors are connected to each other, a manufacturing process can be simplified. Since the biosensors manufactured as described above have the shape in which the plurality of biosensors are connected to each other, the user can carry and use the biosensors by cutting them off one by one whenever the biosensors are used. Cutting grooves may be formed between the biosensors so that the biosensors can be easily cut.

Figure 11:
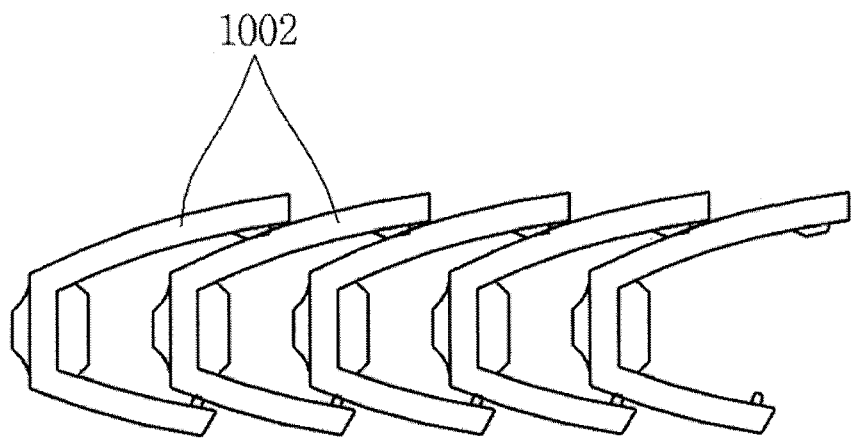
FIG. 11 is a view for explaining a state in which a plurality of biosensors in accordance with another embodiment of the present invention are accommodated.

FIG. 11 is a view for explaining a state in which the plurality of biosensors shown in FIG. 9 are overlapped and accommodated in the case. When the biosensors are overlapped and accommodated in a case (not shown) in a state in which the biomaterial introduction holes 802 are directed downward, the portion A of the detector 602 is pushed into the case so that the biosensor can be easily attached to the detector.

The foregoing description concerns an embodiment of the invention, is intended to be illustrative, and should not be construed as limiting the invention. The present teachings can be readily applied to other types of devices and apparatuses. Many alternatives, modifications, and variations within the scope and spirit of the present invention will be apparent to those skilled in the art.

The invention claimed is:

1. A biomaterial measuring sensor used with a detector to measure a biomaterial, comprising:

a body portion having a recess for holding an end of a detector and a cavity vertically passing through the body portion at the bottom of the recess, wherein the cavity includes a reaction chamber at upper portion thereof, a capillary tube connected to the reaction chamber under the reaction chamber and having a width smaller than the width of the reaction chamber, and a biomaterial introduction hole connected to the capillary tube under the capillary tube, and wherein the body portion is configured to be attached to and detached from the detector; and a sensor portion having a reactive electrode on a lower surface, a reaction reagent fixed onto the reactive electrode and biochemically reacting with the biomaterial, a conductive electrode configured to transmit a signal generated by the biochemical reaction to the detector and positioned on an upper surface which is the opposite surface to the lower surface, and a conductor passing through the sensor portion and electrically connecting the reactive electrode to the conductive electrode, wherein the sensor portion is positioned on the bottom of the recess to cover the reaction chamber and attached to the body portion such that the reactive electrode and the reaction reagent are positioned over and faces the reaction chamber and the capillary tube, and the conductive electrode is exposed to the recess.

2. The biomaterial measuring sensor according to claim 1, wherein the biomaterial introduction hole has a projection shape.

3. The biomaterial measuring sensor according to claim 1, wherein the body portion has a conical or pyramidal shape and the biomaterial introduction hole formed in an apex of the conical or pyramidal shape.

4. The biomaterial measuring sensor according to claim 1, wherein the body portion has an open trapezoidal shape.

5. The biomaterial measuring sensor according to claim 1, wherein the body portion and the detector are attached to each other by a magnetic force.

6. The biomaterial measuring sensor according to claim 4, wherein a side surface of the body portion is attached in a cuttable manner to a side surface of another biomaterial measuring sensor.

7. The biomaterial measuring sensor according to claim 1, wherein the body portion has a hook fastened to the detector.

8. A biomaterial measuring apparatus including a detector and a measuring sensor, wherein the measuring sensor comprises:

a body portion having a recess for holding an end of the detector and a cavity vertically passing through the body portion at the bottom of the recess, wherein the cavity includes a reaction chamber at upper portion thereof, a capillary tube connected to the reaction chamber under the reaction chamber and having a width smaller than the width of the reaction chamber, and a biomaterial introduction hole connected to the capillary tube under the capillary tube, and wherein the body portion is configured to be attached to and detached from the detector; and a sensor portion having a reactive electrode on a lower surface, a reaction reagent fixed onto the reactive electrode and biochemically reacting with the biomaterial, a conductive electrode configured to transmit a signal generated by the biochemical reaction to the detector and positioned on an upper surface which is the opposite surface to the lower surface, and a conductor passing through the sensor portion and electrically connecting the reactive electrode to the conductive electrode, wherein the sensor portion is positioned on the bottom of the recess to cover the reaction chamber and attached to the body portion such that the reactive electrode and the reaction reagent are positioned over and faces the reaction chamber and the capillary tube, and the conductive electrode is exposed to the recess, wherein the detector comprises a connector protruding from the detector and electrically connected to the conductive electrodes when the recess holds the end of the detector.

9. The biomaterial measuring apparatus according to claim 8, wherein the detector further comprises an ejector configured to detach the measuring sensor.

10. The biomaterial measuring apparatus according to claim 8, wherein the connector further comprises a resilient body configured to provide a resilient force in a direction in which the measuring sensor is attached to the detector.

11. The biomaterial measuring apparatus according to claim 8, wherein the detector further comprises a groove fastened to a hook.

12. The biomaterial measuring apparatus according to claim 8, wherein the detector has a magnetic force around the connector.

13. The biomaterial measuring sensor according to claim 1, further comprising:

a sensor fixing portion positioned on the sensor portion in the recess to fix the sensor portion to the body portion, wherein the sensor fixing portion has an opening to expose the conductive electrode of the sensor portion.

14. The biomaterial measuring apparatus according to claim 8, further comprising:

a sensor fixing portion positioned on the sensor portion in the recess to fix the sensor portion to the body portion, wherein the sensor fixing portion has an opening to expose the conductive electrode of the sensor portion.

* * * * *